(12) United States Patent
Laycock et al.

(10) Patent No.: US 8,883,063 B2
(45) Date of Patent: Nov. 11, 2014

(54) MOULD MAT FOR PRODUCING BONE CEMENT PELLETS

(71) Applicant: Biocomposites Limited, Staffordshire (GB)

(72) Inventors: Phillip Laycock, Cheshire (GB); John Cooper, Cheshire (GB); Russell Waters, Cheshire (GB); John Colclough, Staffordshire (GB); Gerhard Maale, Dallas, TX (US)

(73) Assignee: Biocomposites Limited, Keele Staffordshire (GB)

( * ) Notice: Subject to any disclaimer, the term of this patent is extended or adjusted under 35 U.S.C. 154(b) by 137 days.

(21) Appl. No.: 13/680,140

(22) Filed: Nov. 19, 2012

(65) Prior Publication Data

US 2013/0341820 A1   Dec. 26, 2013

(30) Foreign Application Priority Data

Nov. 18, 2011 (GB) .................................. 1119966.8
Jul. 16, 2012 (GB) .................................. 1212627.2

(51) Int. Cl.
| | | |
|---|---|---|
| *B29C 33/42* | (2006.01) | |
| *A61F 2/28* | (2006.01) | |
| *A61L 33/00* | (2006.01) | |
| *A61F 2/46* | (2006.01) | |
| *B27N 5/00* | (2006.01) | |
| *A61F 2/30* | (2006.01) | |

(52) U.S. Cl.
CPC ... *A61L 33/0005* (2013.01); *A61F 2002/30227* (2013.01); *A61F 2/28* (2013.01); *A61F 2310/00353* (2013.01); *A61F 2002/30957* (2013.01); *A61F 2002/2835* (2013.01); *A61F 2/4644* (2013.01); *B27N 5/00* (2013.01)
USPC .................... 264/297.9; 264/297.8; 249/119; 249/126; 249/127

(58) Field of Classification Search
None
See application file for complete search history.

(56) References Cited

U.S. PATENT DOCUMENTS

| | | | | |
|---|---|---|---|---|
| 534,633 | A | * | 2/1895 | Coleman ........................ 249/127 |
| 2,505,947 | A | * | 5/1950 | De Brocke ..................... 249/127 |
| 3,234,609 | A | * | 2/1966 | Madono ......................... 164/121 |
| 3,588,029 | A | * | 6/1971 | Hinds ............................. 249/127 |
| 2012/0032374 | A1 | * | 2/2012 | Bratt et al. .................. 264/328.2 |
| 2014/0031950 | A1 | * | 1/2014 | Cook et al. ................. 623/23.61 |

* cited by examiner

*Primary Examiner* — Mary F Theisen
(74) *Attorney, Agent, or Firm* — Tarolli, Sundheim, Covell & Tummino LLP

(57) ABSTRACT

A means to prepare bone cement pellets comprising bone cement paste which hardens through hydration a flexible mold mat having pellet cavities on both sides and a scraper for pasting the bone cement paste in to the pellet cavities where the paste is allowed to harden.

30 Claims, 8 Drawing Sheets

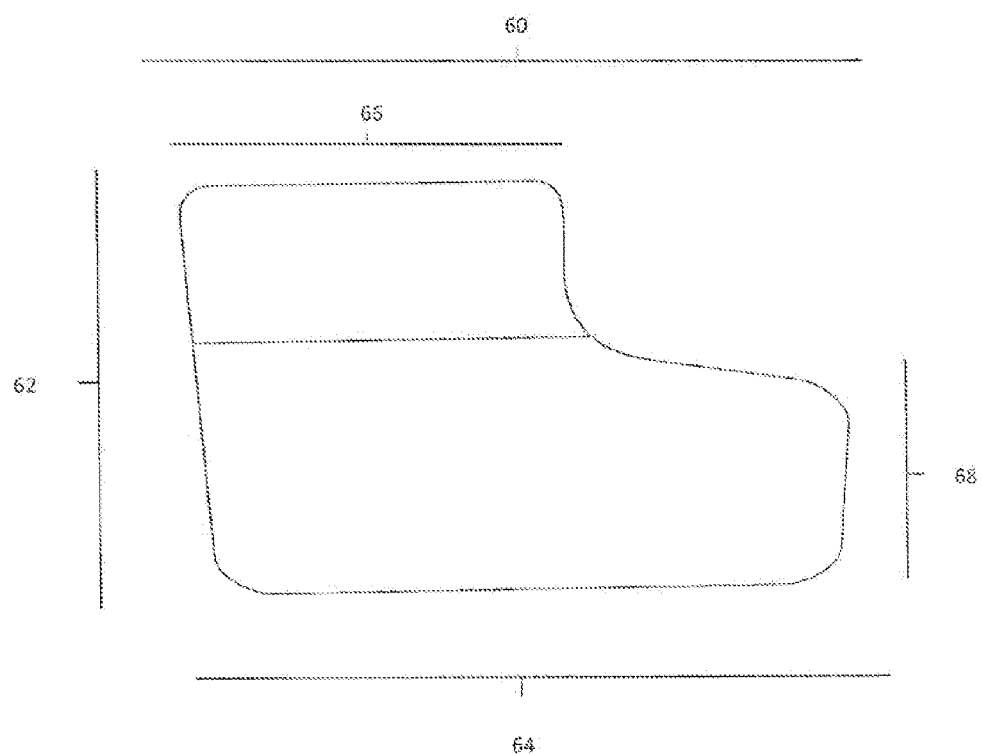

MOULD MAT FOR PRODUCING BONE CEMENT PELLETS

CROSS-REFERENCES TO RELATED APPLICATIONS

The present application claims foreign priority benefits under 35 U.S.C. §119(a)-(d) to currently pending United Kingdom Patent Application No. 1119966.8, filed 18 Nov. 2011, and United Kingdom Patent Application No. 1212627.2, filed 16 Jul. 2012. The present application claims priority to the above-identified patent applications, which are incorporated in their entirety herein by reference for all purposes.

BACKGROUND OF INVENTION

The present invention provides a mould mat and method for producing bone cement pellets, i.e. hardened pellets of a bioabsorbable bone substitute material suitable for the treatment of bone disorders and filling of bony voids or defects of the skeletal system. In particular, although not exclusively, the present invention provides a convenient and simple means to produce moulded, hardened pellets (e.g. cylindrical pellets) of a calcium-based bone cement having a range of sizes for the treatment of bone disorders and filling bone defects, with minimal bone cement wastage.

The use of calcium salt based bone substitute materials is common practice in orthopaedic surgical procedures for the filling of bony voids or gaps of the skeletal system caused by trauma, disease or surgery. These materials when implanted are intended to resorb and be replaced by new bone as they do so. They can consist of a range of different calcium based salts incorporating sulphate and/or phosphate based anions. They may be provided in a range of physical forms including granules and pellets.

There are a number of calcium based bone cement materials which may be used as bone void fillers. These are typically supplied in the form of a powder which when mixed with an aqueous liquid component forms a hardenable cohesive mass that cures and finally sets to form a calcium based bone cement.

It is to be understood that a bone cement is a bone graft or bone substitute material that hydrates, hardens and sets when powder and aqueous liquid components are mixed together. Any bone cement described herein may be used to produce bone cement pellets as disclosed.

Herein, 'bone graft' and 'bone substitute' are terms that are used interchangeably.

Calcium sulphate hemi-hydrate is one such calcium based bone substitute material. When the calcium sulphate hemi-hydrate powder is blended with an appropriate quantity of water or salt solution, the mixture hydrates to form a cohesive mass and sets with a mildly exothermic reaction to give calcium sulphate di-hydrate (i.e. the bone cement) according to the following reaction:

$CaSO_4 \cdot \tfrac{1}{2}H_2O$(Plaster of Paris)+
$1\tfrac{1}{2}H_2O = CaSO_4 \cdot 2H_2O$(gypsum)

The calcium sulphate hemi-hydrate may be used alone or it may be used in combination with calcium phosphate based bone substitute materials including tricalcium phosphate and hydroxyapatite.

Calcium phosphate cement (CPC) is a synthetic bone graft material that was invented in 1986 by L. C. Chow and W. E. Brown, scientists at the American Dental Association. The cement is formed from a calcium phosphate based bone substitute material comprising a white powder consisting of equimolar amounts of ground $Ca_4(PO_4)_2O$ (tetracalcium phosphate, TTCP) and $CaHPO_4$ (dicalcium phosphate anhydrous, DCPA). The powder when mixed with water forms a workable paste which can be shaped during surgery to fit the contours of a wound. The paste hardens (i.e. fully sets) within 20 min to form the calcium phosphate cement, thereby allowing rapid closure of the wound. The hardening reaction, which forms nanocrystalline hydroxyapatite (HA) as the product, is isothermic and occurs at physiologic pH so tissue damage does not occur during the setting reaction.

There are now available a number of different formulations of CPCs. These may contain a range of calcium based salts including monocalcium phosphate, dicalcium phosphate, tetracalcium phosphate, octacalcium phosphate and calcium carbonate and combinations thereof. The calcium based salts are mixed together with an aqueous mixing liquid which may also contain soluble phosphates such as sodium phosphate or phosphoric acid.

Depending upon the surgical procedure being undertaken and the surgeon's preference, it may be required to use the bone cement in the form of pellets or granules. A granular bed of bone graft material contains inter-granule porosity, and this is often considered to be a prerequisite for bony in-growth. The packing density and inter-granule pore size will depend upon the pellet/granule size and size range. A granular or pelletised form of bone graft material also enables the material to be easily mixed with morselised autograft, an often conducted practice in many surgical procedures. The use of moulded pellets having a uniform pellet shape and/or size helps ensure a more predictable resorption profile.

Frequently, therapeutically active compounds are added to the hardenable bone cement which is used as a carrier for the local delivery of the therapeutically active compound. The addition to bone cement and subsequent formation into pellets represents a convenient and effective means to deliver the therapeutically active compound to the site and helps ensure a more consistent and predictable release profile of said compound to the surrounding tissue.

To enable a bone cement to be presented to the surgical site in the form of pellets, some form of pellet mould is required to aid in the formation of the pellets. A mould mat containing a plurality of cavities therein, in which the pellets are shaped, is typically used. This is typically provided as part of a kit of parts for forming the hardenable bone cement pellets. The kit of parts usually contains a powdered bone cement material, a mixing aqueous liquid, a mixing bowl, a mixing spatula, a mould mat and a scraper.

The mould mat typically takes the form of a flat mat made from a flexible rubber or polymeric material, and containing a plurality of cylindrical or hemispherical shaped cavities on one side. The bone cement is prepared in the normal manner by using a small mixing spatula or similar and mixing together all of the powder components with all of the liquid components in a bowl, pot or dish. The resulting intermediate paste (i.e. hardenable bone cement) is then pressed (i.e. pasted) into the pellet cavities, for example by use of a small mixing spatula, where it is allowed to harden and set. Once fully hardened the mould mat can be flexed to extract all pellets from the mould.

Pasting the cement into the cavities of a mould mat of the prior art can be a messy and time consuming procedure, particularly when using the small mixing spatula for this purpose. Additionally, mould mats of the prior art often contain an array of cavities whereby the distance between adjacent cavities is large relative to the cavity diameter, resulting in a large area of the surface of the mat that does not contain any cavities. The cavities are often arranged in rows and columns at right angles to one another. Within the array, the spacing between adjacent cavities within the rows and/or columns can be relatively large compared to the pellet diameter, particularly for smaller diameter pellets. This will mean that there is a relatively larger proportion of the area of the mat, within the array, that does not contain cavities. This has the effect that when bone cement is drawn down the length of the surface of the mat it encounters proportionately more mat-surface (no cavities) than cavity. This, typically, also results in a waste of expensive bone substitute material as it is difficult to ensure that all of the hardenable bone cement is used to fill all of the mould cavities. The use of the small mixing spatula to paste all of the hardening cement into the mould cavities can take longer than the setting time of the cement such that the cement hardens and sets before it is all used to fill the mould cavities. The extraction of the bone pellets through flexing of the mat can be difficult as the mat may not flex very well, or the pellets may become stuck within the mat.

The surgeon therefore is faced with the possibility of having insufficient pellets for the surgical site due to the surgeon being unable to extract some of the pellets from the mould mat of the prior art by flexing it. Those that have been extracted may have rough edges due to the bone cement residue that has been left on the mould mat surface and has hardened.

In order to provide the surgeon with the option to produce a range of pellet sizes, or shapes, and also additional quantity of pellets the mould mat may be excessively large or indeed two mould mats having cavities of differing shapes or sizes may be required. Additional mould mats add to both cost and packaging requirements which can further impact on sterilization issues and storage volumes. There is also an increase of bone cement wastage where bone cement has remained within the area between the cavities on the surface of the mould mat.

The present invention seeks to overcome one or more of the aforementioned technical problems for forming bone cement pellets.

DISCLOSURE OF THE INVENTION

Thus in accordance with a first aspect, the present invention provides a mould mat containing cavities wherein the size, spacing and geometric arrangement of cavities is such that any straight line drawn along the full length of the mat parallel to an edge of the mat in at least one direction and within the arrangement of cavities on the mat will always intersect at least one cavity.

The cavities may be cylindrical or hemispherical in shape cavities and may also be cylindrical in shape and have a hemispherical closed end.

According to one embodiment of the present invention, the spacing and geometric arrangement of the cavities in the mould mat is such that any column of cavities within the arrangement of cavities has a diagonal offset of about 30 degrees relative to the edge of the mould mat. In another embodiment of the present invention, the diagonal offset is about 20 degrees relative to the edge of the mould mat.

The mould mat will typically be made of a flexible polymeric material which is biologically acceptable, such as a silicone rubber or a thermoplastic elastomer (TPE), or any material which will allow the mould mat to be sufficiently flexible so as to allow the surgeon to bend or roll the mat easily to release the bone cement pellets from the cavities in the mould mat. Other suitable biologically acceptable materials for the mould mat will be readily apparent to the skilled person.

A flat device, such as a scraper or spreader, is typically used to fill the cavities with the bone cement. The device may be of a substantially similar width to the mould mat, or alternatively it may be of a similar width to the width of the area occupied by the cavities on the mould mat. This facilitates the rapid and easy filling of the cavities with hardenable bone cement paste. The scraper or spreader device will typically be made from a rigid or semi-rigid material which is biologically acceptable such as a polymeric material including, but not limited to, polypropylene, polyethylene, polyvinyl chloride, polyacetal, or any other mechanically similar material. The scraper or spreader device is typically thicker at the handle part, around about 3 mm to about 4 mm thick, and typically tapers down to around about 1 mm to about 2 mm thickness at its edge where it engages the mat; this allows for ease of handling by the surgeon of the scraper.

A second embodiment of a scraper or spreader device that may be used in accordance with the invention is a flat device having a substantially 'L'-like shape, where the edge of the scraper or spreader device that engages the mould mat is substantially of a similar width to that of the mould mat, or alternatively it may be of a similar width to the width of the area occupied by the cavities on the mould mat. This scraper or spreader device facilitates rapid and easy filling of the cavities with a hardenable bone cement paste. This second embodiment would also be, typically, made from a rigid or semi-rigid material including but not limited to, polypropylene, polyethylene, polyvinyl chloride, polyacetal, or any other mechanically similar material. The top of the 'L' shaped scraper or spreader device is typically thicker as it makes up the handle part of the scraper or spreader device and is typically around 3 mm to about 4 mm thick. This allows for ease of handling by the user, such as a surgeon, of the scraper or spreader device. The scraper or spreader device typically tapers down from the handle to around 1 mm to 2 mm thickness at its edge where it engages the mat.

The 'L' shape of the scraper or spreader device is created due to the handle of the scraper or spreader device having a section removed such that the length of the handle is typically around half to two-thirds of the length of the opposite edge of the scraper or spreader device that engages the mat, such that the scraper or spreader device therefore substantially resembles an 'L'-shape in plan-view.

As a result of this removed section, one of the adjacent sides of the scraper or spreader device, between the handle and the tapered edge, is approximately half the length of its opposing side. This shorter side section of the device may therefore be used to mix the bone cement powder with an aqueous liquid in the mixing pot, and may also then be used to scoop the hardenable bone cement paste from the mixing pot and onto the mould mat prior to spreading it on the mould mat using the tapered edge of the device.

The tapered end of either of the first or second embodiments of a scraper or spreader device as described above that may be used in accordance with the invention, when applied to the mould mat and pulled lengthways down the mould mat cleans away any excess bone cement, substantially eliminating bone cement wastage, as no or very little bone cement will be present on the mould mat surface where no cavity exists. The excess bone cement remains on the scraper therefore allowing it to be easily reapplied to the mould mat. The elimination of bone cement from the surface area of the mould mat means that the pellets easily come out of the mould mat and have a smooth flat surface finish. As there is no cement residue on the mould mat surface area it prevents the extracted pellets from having rough edges.

The mould mat may contain cavities only on one side thereof or in another embodiment it may contain cavities on both sides. According to one embodiment, the mould mat may contain cavities of one size and shape on a first side and cavities of a second size and shape on a second side. Alternatively, the cavities may all be of a similar size and shape, as desired. Each side of the mould mat may contain cavities of two or more sizes and/or shapes. The size of the cavities may be between about 2 mm to about 8 mm in diameter.

The mould cavities in the mould mat are arranged in an array of rows and columns. The rows run across the width of the mould mat, perpendicular to the long edge when the mould mat is not square in shape, while the columns run, generally, along the length of the mould mat.

The position of the cavities in the mould mat is arranged such that their diameters, separation and relative position are all within fixed limits as described below.

The cavities in the mould mat are arranged in an array and spaced such that any straight line drawn along the length of the mould mat, parallel to an edge of the mould mat in at least one direction within the cavity array, will always intersect one or more cavities, typically cavities every row, every alternative row, or every third row. When the mould mat is not square-shaped, the edge in question is always the long edge.

This ensures that the bone cement paste which is being forced length-ways along the surface of the mould mat by the scraper always encounters cavities along the width of the scraper and the full length of the mould mat. This allows for faster and more efficient filling of the cavities which means very limited or substantially no bone cement wastage, hence a more rapid production of pellets is achievable, which is essential if a faster setting material is being used.

According to one embodiment of the invention, the mould mat may comprise cavities on both side of the mat. These cavities may be the same size and shape, or may be different sizes and shapes. Additionally, any one side of the mould mat may contain cavities of different sizes and shapes.

The mould mat has an outer perimeter down both sides of the length and the width of the mat. The perimeter is typically between 5 mm-10 mm from the outer edge of the mat to the start of the arrangement of cavities.

The spacing of the cavities within the cavity array is dictated, to a large extent, by the ability to manufacture the tool necessary to manufacture the mould mat. There is generally a practical limit to the minimum distance between the 'pins' in the tool that is used to manufacture the mould mat by an injection moulding process. For a fixed spacing distance (of pins in the tool or corresponding cavities in the mould mat), the larger the pellet cavity, the larger will be the total area of cavities to the area of the entire cavity array.

Mould mats according to the present invention have a higher ratio of cavity area to area of the cavity array (the cavity-to-total area) for equivalent size cavities than existing mould mats. The cavity-to-total area is typically from about 0.31 to about 0.36 for cavities which are about 3 mm in diameter, from about 0.43 to about 0.49 for cavities which are about 4.8 mm in diameter, or from about 0.50 to about 0.55 for cavities which are about 6 mm in diameter.

By way of comparison, a prior art mould mat (such as that which is depicted in FIG. 7) has a cavity-to-total area of the cavity array of 0.33 for the larger 4.8 mm diameter cavities, and 0.28 for the smaller 3 mm diameter cavities. The mould mat of the instant invention (as depicted in FIGS. 2 and 5) has an array of 3 mm diameter cavities where cavity-to-total area of the cavity array is 0.34, and a cavity-to-total area of the cavity array of 0.47 for the larger 4.8 mm diameter cavities. In both cases, this is considerably larger than the equivalent prior art mould mat. Additionally, the 6 mm diameter cavities shown in FIG. 2 have a cavity-to-total area of the cavity array of 0.51.

In this specification, the following words and expressions, if and when used, have the meanings ascribed below:

"bone cement" means a hardened (i.e. fully set or cured) hardenable bone cement comprising a bioabsorbable bone substitute material suitable for the treatment of bone disorders and filling of bony voids or defects of the skeletal system;

"bone substitute material" means a bioabsorbable material, e.g. calcium sulphate hemihydrate and tricalcium phosphate, which is used for the treatment of bone disorders and filling bony voids or defects of the skeletal system to permit regeneration of natural bone growth in the skeletal system and which is capable of forming a bone cement e.g. when mixed with an aqueous solution;

"comprising" or any cognate word specifies the presence of stated features, steps, or integers or components, but does not preclude the presence or addition of one or more other features, steps, integers, components or groups thereof. The expressions; "consists of" or "consists essentially of" or cognates may be embraced within "comprises" or cognates, wherein "consists essentially of" permits inclusion of substances not materially affecting the characteristics of the composition to which it applies;

"Diagonal offset" means the position of any hole relative to the nearest hole on an adjacent row. This is measured by drawing two lines perpendicular to the row through the centre of each hole. A third line is drawn joining the centre of the two holes. The internal angle by which this third line intersects each perpendicular line indicates the diagonal offset;

"scraper" or "spreader" means a component that is used to apply the hardenable bone cement paste to the mould mat.

"hardenable bone cement" means a composition comprising a bone substitute material as defined herein and a hardening agent, e.g. an aqueous solution, which upon hardening (i.e. fully setting) forms a bone cement as defined herein. Typically, the hardenable bone cement is in the form of a workable paste;

"mould mat" means a generally flat and flexible mat having a plurality of cavities to accept a bone cement in a mouldable paste condition and contain the cement for a time sufficient to allow hardening of the cement to give set pellets prior to their extraction.

"pellet cavity" means a cavity within a mould mat for producing a bone cement pellet.

It is to be understood that use of the terms "mould cavity", "cavity" and "pellet cavity" is interchangeable herein.

BRIEF DESCRIPTION OF DRAWINGS

The various features of the invention, which are applicable as appropriate to all aspects, will now be described in more detail with reference to the following drawings, where:

FIG. 8 is a plan view of the second embodiment of the scraper.

DETAILED DESCRIPTION OF DRAWINGS

A mould mat is disclosed herein along with a scraper which is used to make bone cement pellets of various sizes where bone cement wastage is substantially eliminated from the surface of the mould mat through the use of the scraper.

FIG. 1

Figure 1:
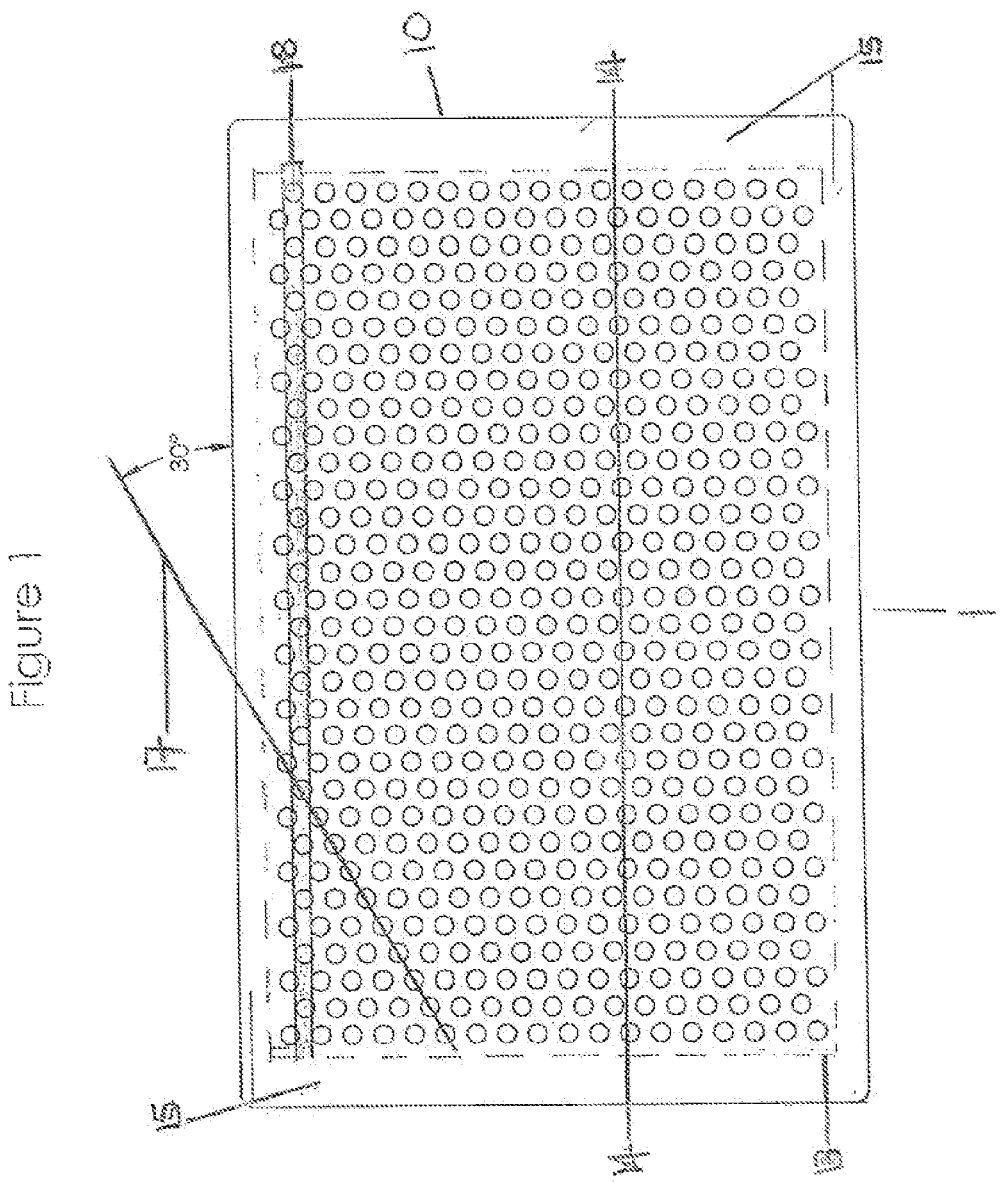
FIG. 1 is a plan view of side one of a mould mat according to an aspect of the present invention. The mould mat of the present invention has pellet cavities on one or both sides of the mould mat.

FIG. 1 shows one side 10 of a mould mat 1, where any straight line 14 drawn along the full length of the mould mat 10 parallel to an edge of the mould mat in at least one direction and within the arrangement of cavities 13 that sit within the perimeter 15 of the mould mat 1 will always intersect at least one cavity 12. It can be seen that any column of cavities 18 within the arrangement of cavities 13 has a diagonal offset of about 30 degrees (denoted by the reference numeral 17) relative to the edge of the mat. The cavities may have a diameter of about 2 mm to about 8 mm.

FIG. 2

Figure 2:
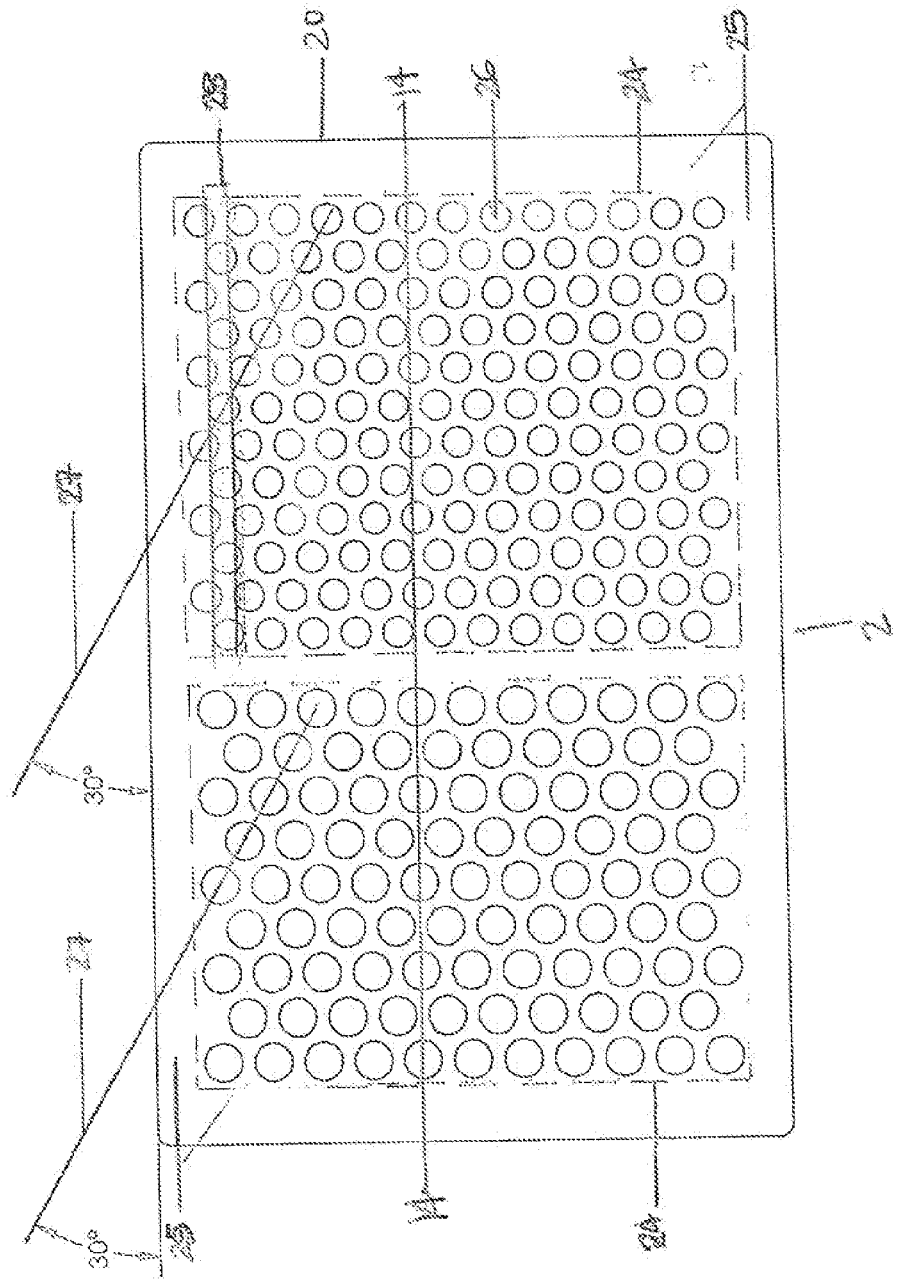
FIG. 2 is a plan view of side two of a mould mat according to an aspect of the present invention.

FIG. 2 shows a second side 20 of a mould mat 2, where any straight line 14 drawn along the full length of the mould mat 20 parallel to an edge of the mould mat 2 in at least one direction and within the arrangement of cavities 24 that sit within the perimeter 25 of the mould mat 2 will always intersect at least one cavity 22. It can be seen that any column of cavities 28 within the arrangement of cavities 24 has a diagonal offset of about 30 degrees (denoted by the reference numeral 27) relative to the edge of the mat. The cavities may have a diameter of about 2 mm to about 8 mm, but it can be seen that in this Figure that the diameters of the cavities 22 are larger than those of the cavities 12 in FIG. 1. Additionally, the cavities 22 shown in FIG. 2 are of different diameters within a single side of the mould mat 2.

FIG. 3

Figure 3:
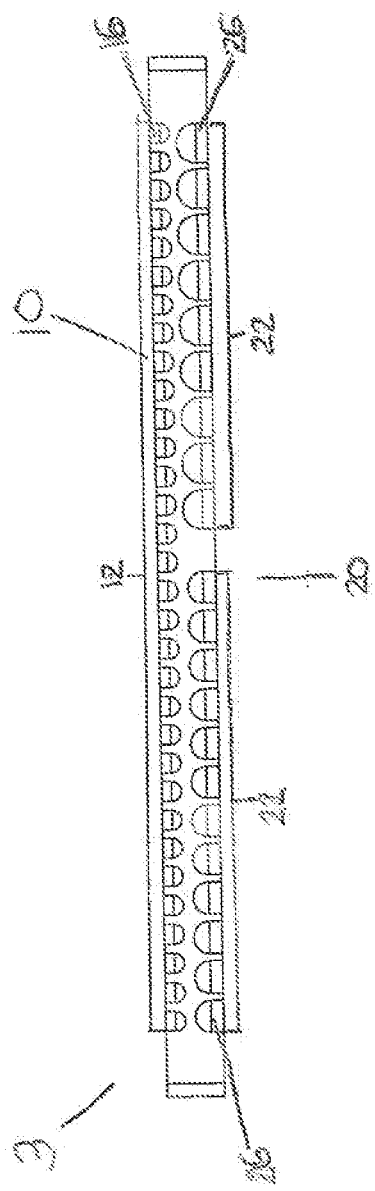
FIG. 3 is a sectional side view of a mould mat according to one of the aspects of the present invention.

FIG. 3 shows a side cross-sectional view of a mould mat 3 that has two sides 10, 20, wherein each side of the mould mat 3 has an arrangement of cavities 12, 22. Thus the cavities 16, 26 within the arrangement of cavities 12, 22 may have a diameter of about 2 mm to about 8 mm.

FIG. 4

Figure 4:
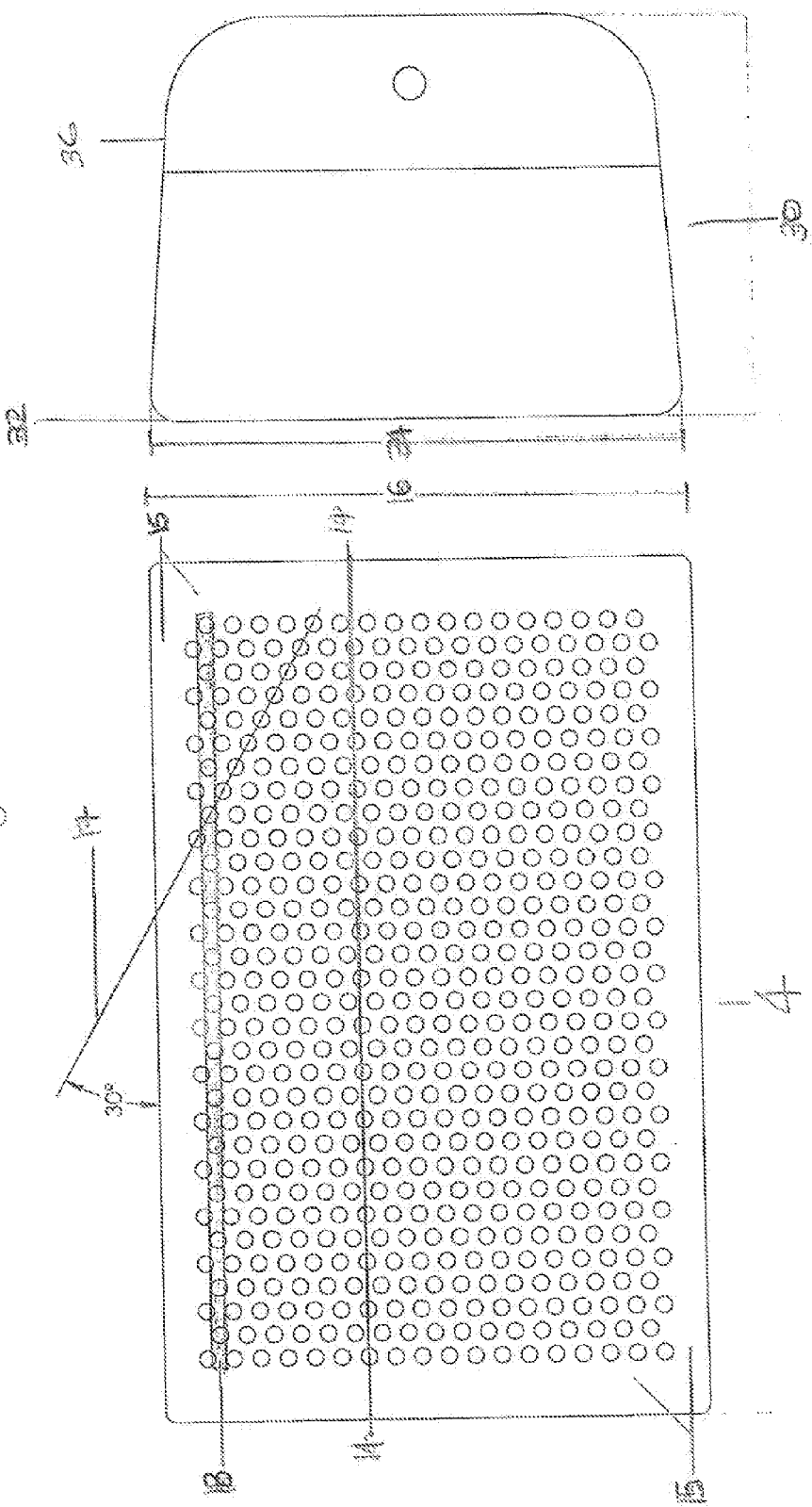
FIG. 4 is a plan view of the mould mat and scraper.

FIG. 4 shows a mould mat 4 and scraper 30 wherein the mat 4, where any straight line 14 drawn along the full length of the mould mat 1 parallel to an edge of the mould mat in at least one direction and within the arrangement of cavities 13 that sit within the perimeter 15 of the mould mat 4 will always intersect at least one cavity 12. It can be seen that any column of cavities 18 within the arrangement of cavities 13 has a diagonal offset of about 30 degrees 17 to the edge of the mat. It is further disclosed a mould mat 10 and scraper 30 wherein the end width 34 of the scraper 30 is substantially the same size as the width 16 of the mould mat 4.

The scraper 30 herein disclosed is typically thicker at the handle part 36 (proximal end), and tapers down 32 (tapered end) to where the scraper engages the mould mat 4. The size of the tapered end 32 is around about 1 mm to about 3 mm, and the width 34 of the tapered end 32 is substantially the same width as the mould mat 4.

FIG. 5

Figure 5:
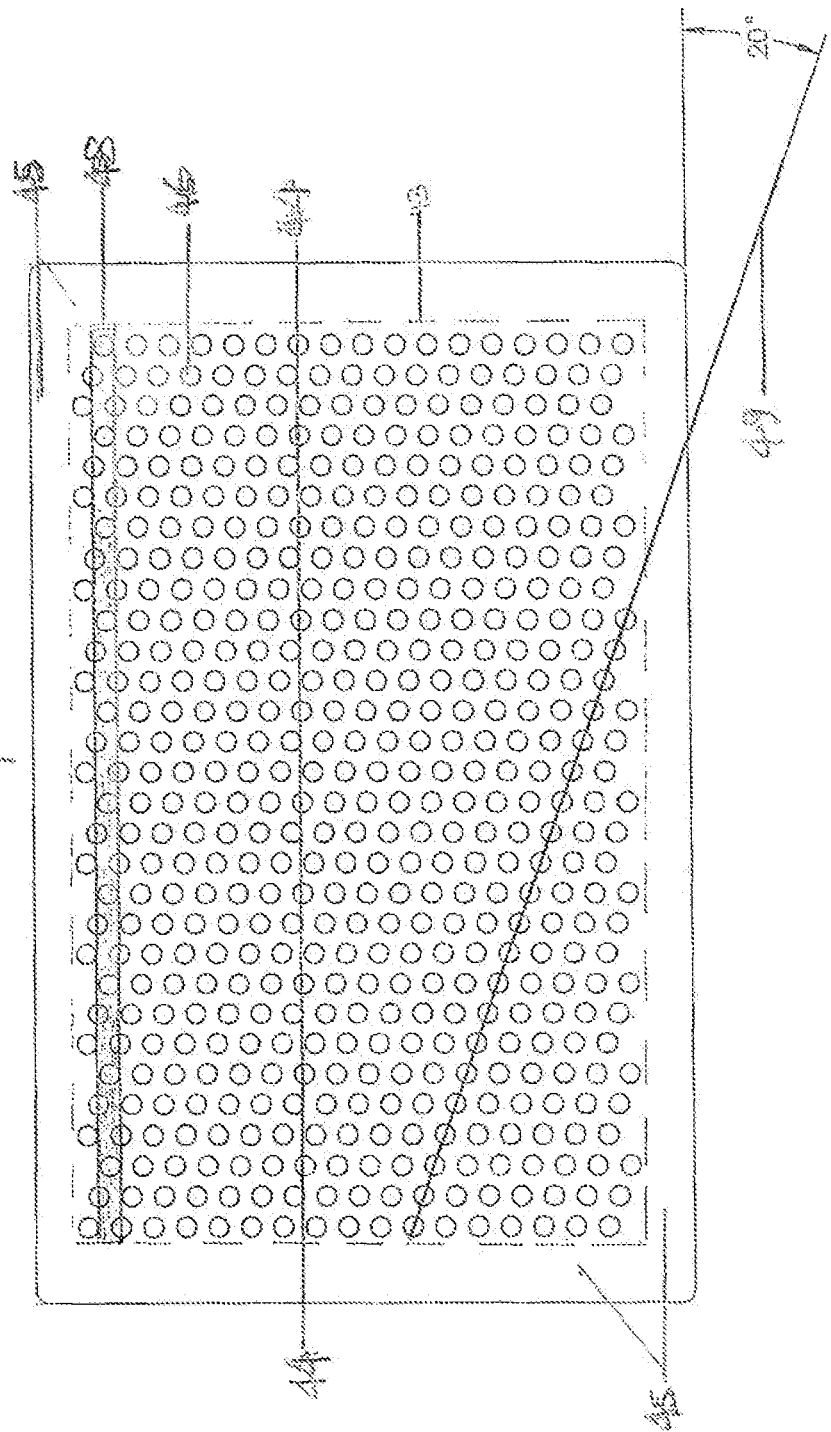
FIG. 5 is a plan view of an alternative embodiment of the present invention.

FIG. 5 shows a mould mat 5, where any straight line 44 drawn along the full length of the mould mat 40 parallel to an edge of the mould mat in at least one direction and within the arrangement of cavities 43 that sit within the perimeter 45 of the mould mat 5, will always intersect a cavity 42. Wherein any column of cavities 48 within the arrangement of cavities 43 has a diagonal offset of about 20 degrees (denoted by the reference numeral 49) relative to the edge of the mat. The cavities may have a diameter of about 2 mm to about 8 mm.

FIG. 6

Figure 6:
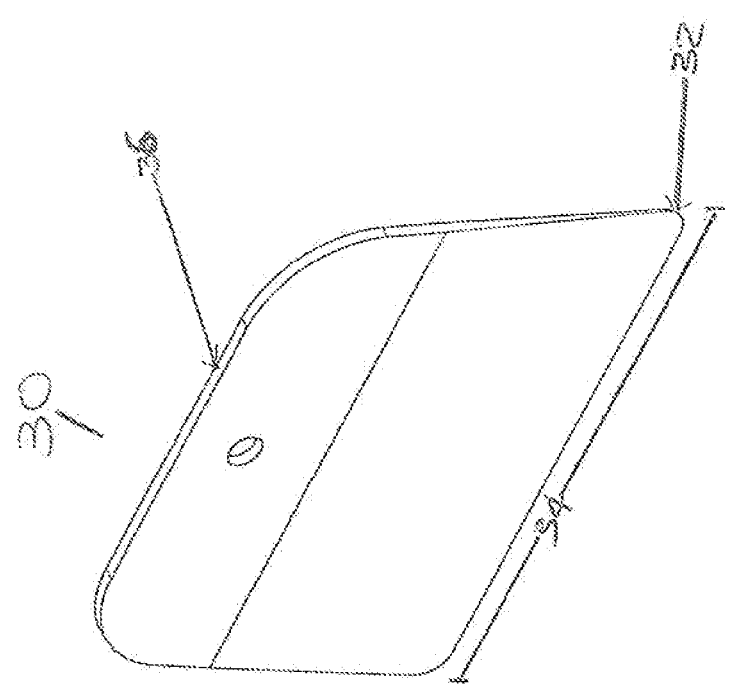
FIG. 6 is a perspective view of the scraper.

FIG. 6 shows a scraper 30. The scraper 30 herein disclosed is typically thicker at the handle part 36 (proximal end) measuring between around about 3 mm to about 4 mm thick and tapers down to the tapered end 32 to where the scraper engages the mould mat. Wherein the thickness of the tapered end 32 is up to around about 1 mm to about 3 mm, and the width 34 of the tapered end 32 is substantially the same width as any given mould mat.

FIG. 7

Figure 7:
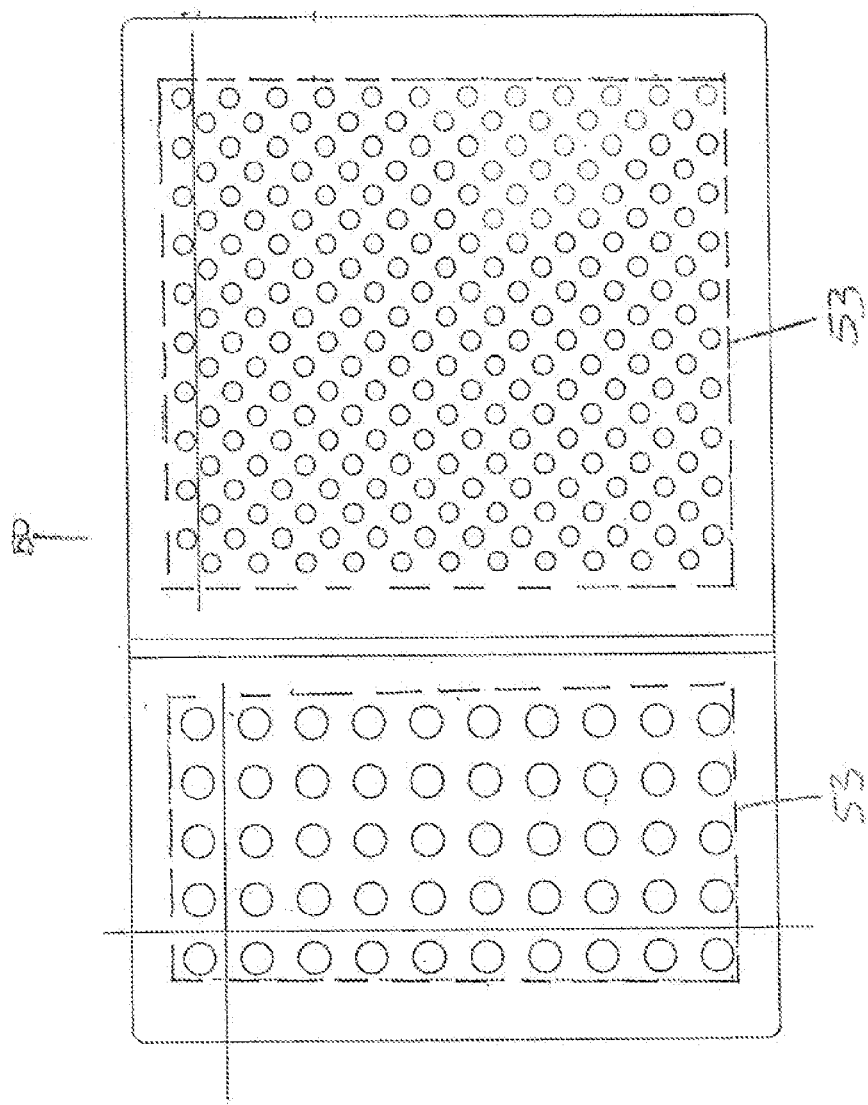
FIG. 7 is a plan view of a mould mat of the prior art.

FIG. 7 shows a typical prior art mat 50 is herein shown for comparison purposes. It can be seen that the arrangement of cavities 53 are such that not every straight line drawn the length of the mat will intersect at least one cavity or a plurality of cavities.

FIG. 8

FIG. 8 shows a further embodiment of a scraper or spreader device 60 according to the invention. The scraper or spreader 60 herein disclosed is typically thicker at the handle part 66 (proximal end) measuring around about 3 mm to about 4 mm thick, tapering down to the tapered end 64 to where the scraper engages the mould mat. The narrower section of the scraper 68 is typically around half the length of the opposite edge of the scraper 62 where the length measures approximately 30 mm to 40 mm and resembles the bottom part of an 'L'-shape. It is this narrower section 68 that may be used to mix the bone cement powder with an aqueous liquid in the mixing pot, and may also then be used to scoop the hardenable bone cement paste from the mixing pot and onto the mould mat prior to spreading it on the mould mat using the edge 64.

A mould mat is thus disclosed where at least one side contains cavities for forming pellets of bone cement, wherein the cavities are arranged such that any straight line drawn the full length of the mould mat in at least one direction within the cavity array and parallel to the long edge (in a non-square shaped mould mat) and within the arrangement of cavities always intersects a plurality of cavities every row, every alternative row or every third row.

Bone Substitute Material

The bone substitute material comprises a calcium salt based bone substitute material.

Typically the bone substitute material is in the form of a solid powder. The bone substitute material when mixed with a hardening agent, for example an aqueous solution (i.e. aqueous salt solution) or water, forms a workable paste (i.e. hardenable bone cement) which on setting/curing forms a hardened, solid bone cement. Suitable calcium salt based bone substitute materials include, but are not limited to, calcium sulphates, calcium phosphates, calcium carbonates and combinations thereof. Preferably, the bone substitute material comprises at least one calcium sulphate, especially calcium sulphate hemihydrate which when mixed with water sets with a mildly exothermic reaction to produce solid calcium sulphate dihydrate.

The at least one calcium based bone substitute material may be used alone or it may be used in combination with one or more calcium phosphate bone substitute materials or calcium carbonates.

Examples of suitable calcium phosphate bone substitute materials include, but are not limited to, monocalcium phosphate, dicalcium phosphate, tricalcium phosphate, tetracalcium phosphate, octacalcium phosphate or hydroxyapatite.

According to one embodiment of the present invention, the bone substitute material comprises a mixture of a calcium sulphate and calcium phosphate bone substitute materials, typically a mixture of calcium sulphate hemihydrate and tricalcium phosphate, more typically beta-tricalcium phosphate.

The bone substitute material, and hence the resulting bone cement pellets, may include a therapeutically active agent. Suitable therapeutically active agents include, but are not limited to, bone inducing growth factors to accelerate bone growth such as bone morphogenetic proteins and parathyroid hormones; bone breakdown inhibitors such as bisphosphonates and osteocalcin; compounds to prevent or treat invasion by foreign living material such as antibiotics, antibacterial compounds, antiviral compounds and antifungal compounds; and anti-inflammatory compounds such as non-steroidal anti-inflammatory compounds (NSAIDs), or combinations thereof. According to one embodiment, the therapeutically active agent comprises an antibiotic.

Alternatively, or additionally, the bone substitute material, and hence resulting bone cement pellets, may include an agent to enhance visualisation of the bone cement in vivo. Suitable agents include, but are not limited to, ionic and non-ionic X-ray contrast agents, typically non-ionic water soluble X-ray contrast agents, such as iodine based media e.g. iohexol.

The therapeutically active agent and/or visual enhancement agent may be included in powder form together with the bone substitute material prior to mixing with the aqueous solution. Alternatively, or additionally, the therapeutically active agent and/or visual enhancement agent may be dissolved or dispersed in the aqueous liquid for mixing with the bone substitute material.

The bone cements pellets produced using the mould mat, as described hereinafter, may be used in surgical procedures to treat bone defects, such as filling bony voids or defects of the skeletal system. The bone cement pellets are packed into the bony void or bony defect where they act as hardened bone substitute material (i.e. a bioabsorbable replacement bone material which acts as a scaffold and promotes the regeneration of natural bone).

EXAMPLES

Example 1

A two sided, flat rectangular mould mat having a width of between 72 mm-122 mm, a length of between 132 mm-179 mm and a thickness of between 6 mm-12 mm was produced using a flexible polymeric material, such as a silicone rubber or a thermoplastic elastomer (TPE). The first side contains an array of 560 cylindrical cavities of 3 mm diameter having a hemispherical closed end arranged in a hexagonal grid pattern with rows of cavities having a diagonal offset of about 30 degrees, as shown in FIG. 1. The second side contains two arrays of cylindrical cavities having a hemispherical closed end, one array consists of 150 cavities of 4.8 mm diameter and the other array consists of 95 cavities of 6 mm diameter. Both arrays are arranged in a hexagonal grid pattern with cavity rows having a diagonal offset of 30 degrees, as shown in FIG. 3.

Example 2

A flat, rectangular mould mat was manufactured from a flexible silicone rubber having dimensions; width=10 cm, length=16 cm, thickness=0.8 cm, where both sides have a plurality of cavities for moulding bone cement pellets. The cavities on both sides are arranged in an array of rows and columns where the rows run across the width of the mould mat and the columns run down the length of the mould mat. Each adjacent row of cavities is offset towards the long edge of the mould mat such that each column of cavities then becomes non-parallel to the long axis of the mould mat. Off-setting each adjacent row by a distance equivalent to approximately half the diameter of a cavity results in the columns aligning with an axis that is approximately about 20 degrees to the long axis of the mould mat. All the cavities on a first side of the mould mat have a diameter of 3 mm and depth of 3.5 mm while all cavities on a second side of the mould mat have a diameter of 4.8 mm and depth of 5 mm. All cavities on both sides of the mould mat are cylindrical in shape and have a hemispherical closed end.

Also included is a semi-rigid scraper or spreader device having a straight, bottom edge of width 9.5 cm, i.e. of a similar width to that of the mould mat. There is thus disclosed a mould mat and a kit of parts enabling the preparation of a plurality of bone cement pellets; the kit comprising a bone cement powder, a mixing aqueous liquid, a mixing bowl, a mixing instrument, a mould mat having cavities on both sides and a scraper or spreader device together with a method of using said kit. The mixing instrument may be a spatula, or the device itself may be used as the mixing spatula to mix the bone cement powder with the aqueous liquid, as described hereinabove.

It is to be understood that various modifications may be made without departing from the scope of the invention, for example:

The number, size, shape and geometric arrangement of the cavities on each side of the mould mat may be different from those described herein.

The pellet geometry may be cylindrical, hemispherical, bullet shaped or ellipsoidal or a combination of these geometries.

The pellet sizes may differ from those disclosed.

The mould mat may be of various geometric shapes including, but not limited to, square, rectangular or circular.

Each and every mould cavity may have an air-escape hole in the bottom or lower half of the cavity to enable escape of air ahead of the cement as it fills the cavity. The air-escape holes may be positioned at the central, lowest point in each cavity and be orthogonal to the surface of the mould mat, exiting the mould mat on the opposite face to the cavity. The holes have a diameter sufficiently small to allow escape of air, but not the considerably more viscous bone cement paste.

The invention claimed is:

1. A mould mat containing cavities wherein the size, spacing and geometric arrangement of cavities is such that any straight line drawn along the full length of the mould mat parallel to an edge of the mould mat in at least one direction and within the arrangement of cavities on the mat will always intersect at least one cavity, wherein the mould mat contains pellet cavities on both sides thereof.

2. A mould mat according to claim 1 wherein any row of cavities within the arrangement of cavities has a diagonal offset of about 30 degrees.

3. A mould mat according to claim 1 wherein any row within the arrangement of cavities has a diagonal offset of about 20 degrees.

4. A mould mat according to claim 1 wherein the mould mat contains pellet cavities of different diameters or shapes on either side thereof.

5. A mould mat according to claim 1 where the cavities are cylindrical in shape.

6. A mould mat according to claim 1 wherein the cylindrical cavities in the mould mat are between about 2 mm to about 8 mm diameter.

7. A mould mat according to claim 1 where the cavities are hemispherical in shape.

8. A mould mat according to claim 7 wherein the hemispherical cavities are between about 2 mm to about 8 mm in diameter.

9. A mould mat according to claim 1 wherein the cavities are cylindrical cavities having a hemispherical closed end.

10. A mould mat according to claim 9 wherein the cylindrical cavities with a hemispherical closed end on the first side are between about 2 mm to about 8 mm in diameter.

11. A mould mat according to claim 1 wherein the mould mat is substantially rectangular in shape.

12. A mould mat according to claim 11 wherein the thickness of the mould mat is between about 6 mm to about 12 mm.

13. A mould mat according to claim 11 wherein the width of the mould mat is between about 72 mm to about 122 mm.

14. A mould mat according to claim 11 wherein the length of the mould mat is between about 130 mm to about 180 mm.

15. A mould mat according to claim 1 wherein it comprises a flexible polymeric material.

16. A mould mat according to claim 14 wherein the flexible polymeric material comprises a silicone rubber and/or a thermoplastic elastomer (TPE).

17. A kit of parts comprising a bone cement powder, a mixing aqueous liquid, a mixing bowl, a mixing instrument, a mould mat according to claim 1 and a device for filling the cavities in the mould mat.

18. A kit of parts according to claim 17 wherein the width of the device substantially matches the width of the mould mat or the width of the arrangement of cavities on the mould mat.

19. A kit of parts according to claim 17 wherein the thickness of the device is about 2.0 mm to about 4.0 mm at one edge thereof.

20. A kit of parts according to claim 19 wherein the device tapers down from the one edge to an opposite edge and has a thickness of about 0.5 mm to about 2.0 mm at the thinner opposite edge.

21. A kit of parts according to claim 17 wherein the device can itself also be used as the mixing instrument.

22. A kit of parts according to claim 17 wherein the device is made of a semi-rigid material.

23. A kit of parts according to claim 22 wherein the semi-rigid material is a polymeric material selected from polyethylene, polypropylene, polyvinyl chloride or polyacetal.

24. A method of producing a plurality of bone cement pellets comprising mixing a bone cement powder with an aqueous liquid, and filling the cavities in a mould mat according to claim 1.

25. A method according to claim 24 wherein the method involves using a kit of parts according to claim 17 for producing a plurality of bone cement pellets comprising:
   providing a kit including a bone cement powder, a mixing aqueous liquid, a mixing bowl, a mixing instrument, a mould mat according to claim 1, and a device for filling the cavities in the mould mat;
   mixing the bone cement powder with an aqueous liquid; and
   filling the cavities in the mould mat.

26. A method according to claim 24 wherein the cavities are filled using a device having a width that substantially matches the width of the mould mat or the width of the arrangement of cavities on the mould mat.

27. A method according to claim 26 wherein the thickness of the device is about 2 mm to about 3 mm at one edge thereof.

28. A method according to claim 27 wherein the device tapers down from the one edge to an opposite edge and has a thickness of about 0.5 mm to about 1.5 mm at the thinner opposite edge.

29. A method according to claim 26 wherein the device is made of a semi-rigid material.

30. A method according to claim 29 wherein the semi-rigid material is a polymeric material selected from polyethylene, polypropylene, polyvinyl chloride or polyacetal.

* * * * *